United States Patent [19]

Hansen, Jr. et al.

[11] Patent Number: 4,514,332
[45] Date of Patent: Apr. 30, 1985

[54] TETRAPEPTIDE ADAMANTYL AMIDES

[75] Inventors: Donald W. Hansen, Jr., Chicago; John S. Baran, Winnetka; William H. Owens, Arlington Heights, all of Ill.

[73] Assignee: G. D. Searle & Co., Skokie, Ill.

[21] Appl. No.: 600,650

[22] Filed: Apr. 16, 1984

[51] Int. Cl.$^3$ .................................. C07C 103/52
[52] U.S. Cl. .................. 260/112.5 E; 260/112.5 R
[58] Field of Search .................. 260/112.5 E, 112.5 R

[56] References Cited

U.S. PATENT DOCUMENTS 4,273,704  6/1981  Mazur .......................... 260/112.5 E

OTHER PUBLICATIONS

Goodman and Gilman, *The Pharmacological Basis of Therapeutics*, (New York, 1975), Fifth Edition, Chaps. 26, 27, 28, 30, 33, 39, 40.

Poulsen, Burton, and Haber, "Competitive Inhibitors of Renin; *Biochemistry*, 12, 3877–3882 (1983).

Burton, Cody, Herd, and Haber, "Specific Inhibition of Renin by An Angiotensinogen Analog...", *Proc. Natl. Acad. Sci. USA*, 77, 5476–5479, (1980).

Cody, Burton, Evin, Poulsen, Herd, and Haber, "A Substrate Analog Inhibitor of Renin That Is Effective In Vivo," *Biochem. Biophys. Res. Commun.*, 97, 230–235, (1980).

Burton, Poulsen, and Haber, "Competitive Inhibitors of Renin...", *Biochemistry*, 14, 3892–3898, (1975).

Haas, Lewis, Scipione, and Koshy, "Micromethod for the Assay of Renin of Seven Species," *Hypertension*, 1, 112–117, (1979).

*Primary Examiner*—Delbert R. Phillips
*Attorney, Agent, or Firm*—John J. McDonnell

[57] ABSTRACT

This invention relates to novel tetrapeptide adamantyl amides that are useful in the treatment of hypertension.

23 Claims, No Drawings

TETRAPEPTIDE ADAMANTYL AMIDES

BACKGROUND OF THE INVENTION (a) Field of the Invention

This invention relates to novel tetrapeptide amides of Formula I that are useful in the treatment of hypertension.

Hypertension is a condition caused by any of a variety of functional abnormalities. For example, hypertension may be related to abnormalities in adrenergic, cholinergic, or neuromuscular interactions; in hormonal balance; or in kidney function, which malfunctions often are caused by abnormalities of the other systems. Treatment with drugs that are intended to act at some receptor site involved in one of the malfunctioning systems has frequently been the basis of therapy. For example, numerous neural receptor blockers are known to act as antihypertensive agents, and diuretics are commonly used to counteract the effects of fluid retention associated with kidney dysfunction. Each of these regimens, however, is associated with side effects often related to inadequate specificity. See generally L. S. Goodman and A. Gilman, eds. *The Pharmacological Basis of Therapeutics* (New York, 1975), Fifth Edition, Chaps. 26, 27, 28, 30, 33, 39, 40.

The renin-angiotensin system has been implicated in hypertension. See Goodman and Gilman, supra, pp. 630–637. The enzyme renin converts the plasma protein angiotensinogen to the essentially inactive decapeptide angiotensin I, which in turn is proteolytically converted by the so-called "converting enzyme" to the potently vasoactive octapeptide angiotensin II. Various peptidases further octapeptide angiotensin II to essentially inactive peptide fragments. In addition to regulating blood pressure, angiotensin also stimulates the secretion of aldosterone and thus is intimately involved in regulating the sodium-potassium balance. Thus, inhibition of renin could be an important means of controlling high blood pressure. Certain short-chain peptide analogs of angiotensinogen segments have been reported to inhibit renin activity. K. Poulsen, J. Burton, and E. Haber, *Biochemistry*, 12, 3877–3882 (1973); J. Burton, K. Poulsen, and E. Haber, *Biochemistry*, 14, 3892–3898 (1975); J. Burton, R. J. Cody, Jr., A. J. Herd, and E. Haber, *Proc. Natl. Acad. Sci. U.S.A.*, 77, 5476–5479 (1980). Peptide inhibitors of renin activity have also been reported to lower blood pressure in primates. See J. Burton, R. J. Cody, Jr., A. J. Herd, and E. Haber, *Proc. Natl. Acad. Sci. U.S.A.*, 77, 5476–5479 (1980); R. J. Cody, J. Burton, G. Evin, K. Poulsen, J. A. Herd, and E. Haber, *Biochem. Biophys. Res. Commun.*, 97, 230–235 (1980). The present invention provides peptide amides of shorter length which are renin inhibitors and exhibit antihypertensive activity.

(b) Prior Art

Certain N-adamantane-substituted tetrapeptide amides are known. U.S. Pat. No. 4,273,704, having the same assignee as the present invention, relates to analgesic tetrapeptide amides having optionally substituted tyrosine as the N-terminal amino acid residue. Although the tyrosine-containing compounds disclosed in the U.S. Pat. No. 4,273,704 exhibit renin inhibitory activity, none of the compounds of the present invention contain aromatic substitution in the N-terminal amino acid residue and the antihypertensive activity has not previously been disclosed.

SUMMARY OF THE INVENTION

The invention relates to compounds of Formula I:

$$R^4NH-\underset{R^2}{\underset{|}{C}}-CONHCHCONHCH_2CONHCHCO-NH-Ad \quad\quad I$$

with substituents $R^1$, $(CH_2)_nS(O)_m-R^3$, and $CH_2C_6H_5$ on the respective α-carbons.

wherein $R^1$ is:
(a)

(CH$_2$)$_p$—cyclopentyl/cyclohexyl ring;

or
(b) straight or branched chain alkyls of 1 to 6 carbon atoms, inclusive;
wherein $R^2$ is:
(a) hydrogen; or
(b) alkyl of 1 to 3 carbon atoms, inclusive;
wherein $R^3$ is:
(a) $CH_2C_6H_5$; or
(b) alkyl of 1 to 3 carbon atoms, inclusive;
wherein $R^4$ is:
(a) hydrogen; or
(b) alkyl of 1 to 6 carbon atoms, inclusive;
wherein $m$ is 0, 1, or 2;
wherein $n$ is 1 or 2;
wherein $p$ is 0, 1, or 2;
and the stereochemical configuration of each of the optically active amino acid residues may independently be D, L or DL; and the pharmacologically acceptable salts thereof.

Examples of alkyl are methyl, ethyl, propyl, butyl, pentyl, hexyl, and the isomeric forms thereof.

Examples of pharmacologically acceptable acid addition salts include the hydrochloride, hydrobromide, hydroiodide, sulfate, phosphate, acetate, propionate, lactate, maleate, malate, succinate, and tartrate salts.

DESCRIPTION OF THE INVENTION

The compounds of this invention may be prepared by any number of methods known to those skilled in the art. For example, the particular sequence of reactions by which the individual amino acids are joined to form the compounds of Formula I is generally not of critical importance, being chosen principally for convenience or for maximum yields. Moreover, the choice of activating reagents and conditions for joining amino acids or small peptides is not limited to those specifically described herein. Peptide intermediates and products of this invention are typically purified by crystallization, where possible, or by column chromatography. Furthermore, where racemic amino acid starting materials are employed, intermediates and products may be separated during chromatography into diastereomers. The accompanying Schemes are used to illustrate one of the possible methods used to prepare the compounds of this invention.

Scheme A illustrates a general method for forming intermediates useful in the synthesis of compounds of Formula I.

SCHEME A

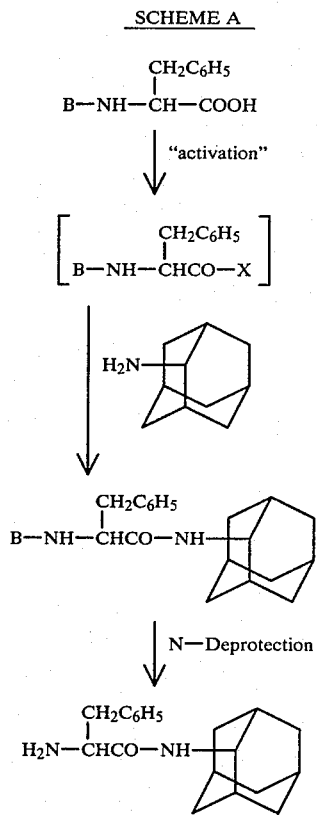

Partially blocked amino acids of Formula II, in which B represents common N-protecting groups such as t-butoxycarbonyl, may be activated by any of several methods known to those skilled in the art. The generally preferred method includes forming a mixed anhydride by reaction with an alkyl chlorocarbonate in an unreactive solvent containing a tertiary amine. Preferred conditions include cooling a mixture of the appropriate compound of Formula II in cold (ca. −30° to −40°) dimethylformamide or dichloromethane containing N-methylmorpholine, followed by addition of isobutyl chloroformate. Once the mixed anhydride of Formula III (X=OCOOCH$_2$CH(CH$_3$)$_2$) has formed, 1- or 2-aminoadamantane (Formula IV) is added and the reaction allowed to proceed at room temperature, giving the fully blocked intermediate of Formula V.

An alternative method of activation employing carbodiimide activation may also be employed to prepare compounds V. For this method, compounds of Formulas III and IV are stirred together in an unreactive solvent, such as dichloromethane, to which is then added a carbodiimide, such as dicyclohexylcarbodiimide. The isolated intermediates, Formula V, are used exactly the same as those formed by the mixed anhydride method.

Using methods appropriate for the particular protecting group B, compounds of Formula V may readily be deprotected to give compounds of Formula VI. Where the t-butoxycarbonyl protecting group is used, for example, preferred deblocking conditions include acid solvolysis in acetic acid containing hydrogen chloride-dioxane. Typically, the resulting hydrochloride salts may be used in subsequent reactions without first isolating the free amine.

Scheme B illustrates one method for extending the peptide chain to form intermediates of Formula XII.

SCHEME B

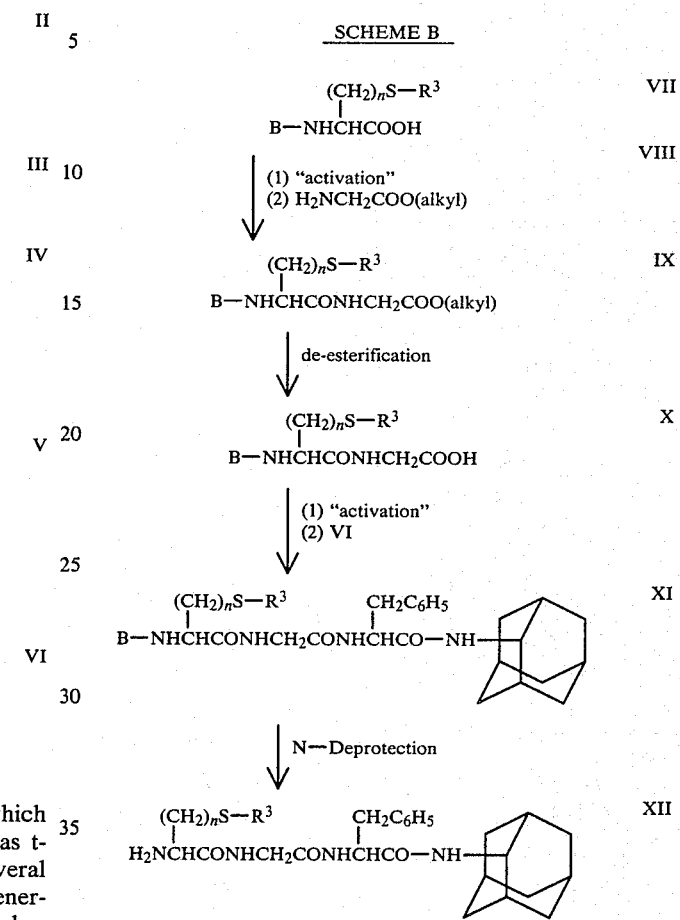

Using methods described above and illustrated in Scheme A, fully protected intermediates of Formula IX are formed from N-protected amino acids of Formula VII and glycine esters, Formula VIII. Hydrolysis of these intermediates, Formula IX, affords the analogous acids of Formula X. Preferred hydrolysis conditions include approximately two-fold potassium hydroxide in aqueous tetrahydrofuran, followed by neutralization with sodium bisulfate. Using the methods described above, compounds of Formula X are activated and then coupled with intermediates of Formula VI to form protected peptides of Formula XI. As described above and illustrated in Scheme A, removal of protecting groups B affords amino compounds of Formula XII.

Scheme C illustrates one method for completing the extension of the peptide chains.

SCHEME C

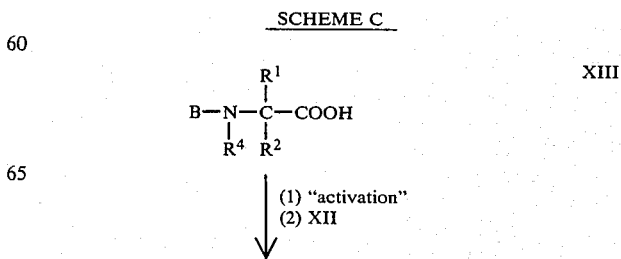

-continued
SCHEME C

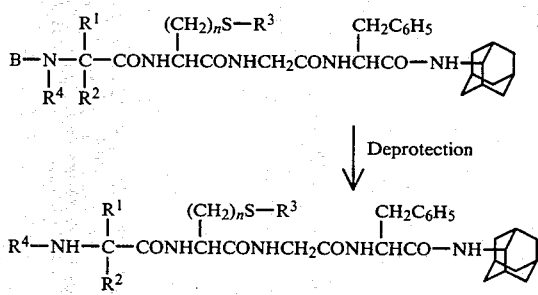

As described above and illustrated in Schemes A and B, suitably protected amino acids of Formula XIII are activated, for example by using mixed anhydride or carbodiimide methods, and allowed to react with intermediates of Formula XII. Appropriate removal of protecting groups from the resultant compounds of Formula XIV affords compounds of this invention, Formula XV (i.e., Formula I wherein m=0).

Scheme D illustrates one method for preparing sulfoxide or sulfone members of this invention, Formula XVI (i.e., Formula I wherein m=1 or m=2, respectively), which for practical reasons are generally prepared after methionine-containing peptides of Formula XV have been fully formed as described above. Preferred oxidizing conditions include hydrogen peroxide in aqueous methanol—at room temperature, sulfoxides are the predominant or sole oxidation product, whereas at elevated temperatures (e.g., refluxing solvent), sulfones are formed.

SCHEME D

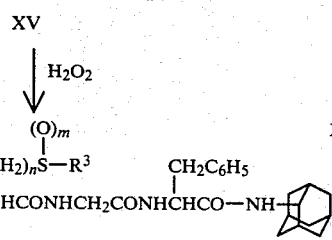

In the aforementioned schemes, the groups $R^1$, $R^2$, $R^3$, and $R^4$ and the quantities m and n are as previously described herein.

The preferred embodiments of this invention include compounds of the following general structure, Formula XVII:

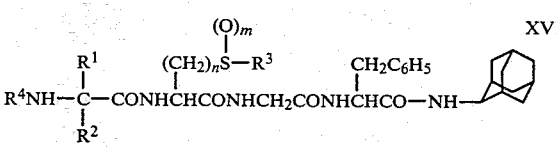

wherein $R^1$ is:
(a)

or
(b) straight or branched chain alkyls of 1 to 6 carbon atoms, inclusive;
wherein $R^2$ is:
 (a) hydrogen; or
 (b) methyl;
wherein $R^3$ is:
 (a) $CH_2C_6H_5$, provided n is 1; or
 (b) alkyl of 1 to 3 carbon atoms, inclusive, provided n is 2;
wherein $R^4$ is
 (a) hydrogen; or
 (b) alkyl of 1 to 6 carbon atoms, inclusive;
wherein m is 0, 1, or 2;
and the sterochemical configuration of each of the optically active amino acid residues may independently be D, L, or DL; and the pharmacologically acceptable salts thereof.

The most preferred embodiments of this invention include compounds of the following general structure, Formula XVIII:

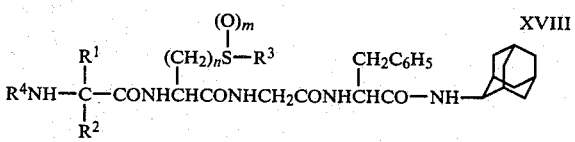

wherein $R^1$ is:
(a)

(b) isobutyl;
(c) sec-butyl; or
(d) isopropyl;
wherein $R^2$ is:
 (a) hydrogen; or
 (b) methyl;
wherein $R^3$ is:
 (a) $CH_2C_6H_5$, provided n is 1; or
 (b) methyl, provided n is 2;
wherein $R^4$ is:
 (a) hydrogen; or
 (b) alkyl of 1 to 6 carbon atoms, inclusive;
wherein m is 0 or 1;
and the sterochemical configuration of each of the optically active amino acid residues may independently be D, L, or DL; and the pharmacologically acceptable salts thereof.

The renin inhibition activity of the compounds of this invention illustrated in the examples was tested by the following method. Pepstatin and the octapeptide prolylhistidylprolylphenylalanylhistidylleucylphenylalanylvalyltyrosine (or, "Pro-[Phe⁶]octapeptide"; see J. Burton, K. Poulsen, and E. Haber, *Biochemistry*, 14, 3892-3898 (1975)) are active in this assay.

Inhibition of Human Renin

International reference standard human renin, isolated from kidneys, was obtained from the World Health Organization International Laboratory for Biological Standards (National Institute for Biological Standards and Control, London, England). Renin activity is defined in "Goldblatt units" (GU), the quantity that, when injected directly into the blood stream of an unanesthetized dog, raises the direct mean femoral artery blood pressure by 30 mm Hg in about two minutes. E. Haas, L. Lewis, P. Scipione, and T. J. Koshy, *Hypertension*, 1, 112–117 (1979). Human angiotensinogen was used as an unisolated component of human blood plasma. The enzyme inhibition assay, see K. Poulsen, J. Burton, and E. Haber, *Biochemistry*, 12, 3866–3882 (1973), involved a two-hour incubation at 37° C. of the following final concentrations of reagents (0.25 ml total volume): 0.1 mGU/ml human renin; 0.05 ml human plasma; 6 mM disodium EDTA; 2.4 mM phenylmethylsulfonyl fluoride and 1.5 mM 8-hydroxyquinoline (angiotensinase inhibitors); 0.4 mg/ml bovine serum albumin; and 0.024 neomycin sulfate in 100 mM Tris-acetate buffer (pH 7.5). The enzymatic reaction was terminated by boiling the mixture for ten minutes. The quantity of angiotensin I formed was determined by radioimmunoassay, using the general method used in the angiotensin I radioimmunoassay kit of New England Nuclear. Test compounds were considered active if inhibition was greater than 20%.

The following tests illustrate the in vivo antihypertensive activities of the compounds of this invention.

Spontaneously Hypertensive Rat Assay—Indirect Measurement

Male spontaneously hypertensive rats were used in this assay. Initial systolic blood pressure was measured using a caudal plethysmograph immediately before administration of test compounds. For initial screening the test compounds were administered intragastrically at a dose of 50 mg per kg of body weight. Blood pressure readings were obtained at four hours (and in some cases also at 24 hours) after dosing. A compound was rated active if the post-treatment blood pressure was significantly depressed ($P \leq 0.05$) relative to the initial pressure reading.

Spontaneously Hypertensive Rat Assay—Direct Measurement

Male spontaneously hypertensive rats were used in this assay. Using a previously implanted arterial catheter, initial mean arterial blood pressure was measured directly immediately before administration of test compounds. For initial screening the test compounds were administered intragastrically at a dose of 50 mg per kg of body weight. Blood pressure readings were usually obtained at 1, 2, 3, and 4 hours after dosing. A compound was rated active if the mean post-treatment blood pressure was significantly different ($P \leq 0.05$) from that of the concurrent placebo control group.

Renal-ligated Hypertensive Rat Assay

Male Sprague Dawley rats aged 11 to 15 weeks old were used in this test. Three hours after bilateral ligation of the renal arteries, the mean arterial blood pressure (measured directly with previously implanted arterial catheters) and the plasma renin activity increased significantly ($P \leq 0.05$) higher than in sham-operated animals. Test compounds were administered intraarterially at a dose of 10 mg per kg of body weight, and blood pressure changes were monitored directly at 5, 10, and 15 minutes after injection. A compound was considered active if the post-treatment blood pressure was significantly ($P \leq 0.05$) depressed relative to the placebo control. Under these test conditions pepstatin significantly reduced both mean arterial blood pressure and plasma renin activity.

Rhesus Monkey Blood Pressure Test

Rhesus monkeys were sodium depleted by means of a fruit diet in combination with intramuscular furosemide injections (0.5 mg per kg of body weight) given twice daily for four days. This procedure causes blood pressure to become dependent on plasma renin activity. J. Burton, R. J. Cody, Jr., A. J. Herd, and E. Haber, *Proc. Natl. Acad. Sci. U.S.A.*, 77, 5476–5479 (1980). On the fifth day the animals were anesthetized with ketamine (100 mg administered intravenously). The femoral artery was cannulated for blood pressure measurement and a percutaneous venous cannula was inserted for test compound administration. The animals were allowed to recover from anesthesia and were restrained in a transparent plastic chair. Blood pressure was monitored continuously both before and after test compounds were administered (at 3 mg per kg of body weight). A compound was considered active if post-treatment mean blood pressure was significantly ($P \leq 0.05$) depressed relative to preadministration mean blood pressure. Under these test conditions captopril at 0.1 mg per kg and "renin inhibitory peptide" (RIP, or prolylhistidylprolylphenylalanylhistidylphenylalanylphenylalanylvalyltyrosyllysine; see Burton et al., supra) at 1.0 mg per kg significantly lowered mean blood pressure.

By virtue of the antihypertensive activity, the compounds of Formula I are useful in treating high blood pressure in mammals. A physician or veterinarian of ordinary skill can readily determine whether a subject exhibits hypertension. Regardless of the route of administration selected, the compounds of the present invention are formulated into pharmaceutically acceptable dosage forms by conventional methods known to those skilled in the art. The compounds may be formulated using pharmacologically acceptable acid addition salts. Moreover, the compounds or their salts may be used in a suitable hydrated form.

The compounds can be administered in such oral dosage forms as tablets, capsules, pills, powders, or granules. They may also be administered intravascularly, intraperitoneally, subcutaneously, or intramuscularly, using forms known to the pharmaceutical art. In general, the preferred form of administration is oral. An effective but non-toxic quantity of the compound is employed in treatment. The dosage regimen for preventing or treating hypertension with the compounds of this invention is selected in accordance with a variety of factors, including the type, age, weight, sex, and medical condition of the patient; the severity of the hypertension; the route of administration; and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the compounds of the invention are ordinarily in the range of 1.0 to 20 mg/kg up to about 100 mg/kg.

The following examples further illustrate details for the preparation of the compounds of this invention. The invention, which is set forth in the foregoing disclosure, is not to be construed or limited either in spirit or in scope of these examples. Those skilled in the art will readily understand that known variations of the conditions and processes of the following preparative procedures can be used to prepare these compounds. All temperatures are degree celsius unless otherwise noted.

PREPARATION OF STARTING MATERIALS AND INTERMEDIATES

Preparation 1 t-butoxycarbonyl-N-(2-adamantyl)-L-phenylalaninamide

To a cold (ca. −78°) solution of 106 g (0.4 mole) of t-butoxycarbonyl-L-phenylalanine (Boc-Phe) and 88 ml (ca. 0.8 mole) of N-methylmorpholine in 300 ml of dichloromethane, stirred over 30 g of 4 A molecular sieves, was added dropwise 52.4 ml (ca. 0.4 mole) of isobutyl chloroformate. The mixture was allowed to warm slowly to 5° and then recooled to about −78°. After adding 75 g (0.4 mole) of 2-aminoadamantane, the mixture was allowed to warm to room temperature and to stir overnight. The mixture was clarified by filtration and washed with several portions of 0.5M sodium bisulfate. The organic layer was heated at reflux over activated charcoal, filtered, dried over sodium sulfate, and concentrate in vacuo to dryness. The resultant title compound was used without further purification in subsequent reactions.

Preparation 2

N-(2-adamantyl)-L-phenylalaninamide hydrochloride

To a stirred solution of 100 g (0.25 mole) of the title product of Preparation 1 in 827 ml of acetic acid was added 413 ml (2.5 mole) of 6.07N hydrogen chloride in dioxane. After about thirty minutes the solution was concentrated in vacuo to a viscous oil. Trituration with diethyl ether afforded a solid which was collected by filtration, washed with diethyl ether, and air dried. Repetition of the trituration with diethyl ether afforded the title compound as an analytically pure solid.

$[\alpha]_D$ +47.5°; $[\alpha]_{365}$ +186.3° (methanol).

Analysis calcd. for $C_{19}H_{26}N_2O \cdot HCl \cdot \frac{1}{4}H_2O$: C, 67.24; H, 8.17; N, 8.28; Cl, 10.44. Found: C, 67.06; H, 8.16; N, 8.24; Cl, 10.33.

Preparation 3 t-butoxycarbonyl-D-methionylglycine methyl ester

The title compound was prepared by the general method of Preparation 1 using 198 g (0.79 mole) of t-butoxycarbonyl-D-methionine (Boc-D-Met) and 99.5 g (0.79 mole) glycine methyl ester (Gly-OMe) hydrochloride. The title compound was isolated as an analytically pure solid without further purification.

$[\alpha]_D$ +7.9°; $[\alpha]_{365}$ +23.6° (methanol).

Analysis calcd. for $C_{13}H_{24}N_2O_5S$: C, 48.73; H, 7.55; N, 8.74; S, 10.01. Found: C, 48.88; H, 7.65; N, 8.53; S, 10.16.

Preparation 4 t-butoxycarbonyl-D-methionylglycine

The title product of Preparation 3 (100 g, 0.31 mole) was dissolved in 800 ml of tetrahydrofuran to which was then added 42 g (0.62) mole of potassium hydroxide dissolved in 2 l of water. After hydrolysis was complete—about two hours at room temperature—the mixture was diluted with about 1 l of dichloromethane and acidified (ca. pH 3) with about 1.1 l of 0.5M sodium bisulfate. The aqueous layer was separated and washed with dichloromethane, and all organic layers were recombined. This organic solution was further washed with water, treated with activated carbon, filtered, dried over sodium sulfate, refiltered, and concentrated in vacuo to an oil. Trituration with diethyl ether afforded a solid which was collected by filtration, washed with diethyl ether, and dried, giving 73 g of analytically pure title compound, m.p. 124.5°–125.5°.

Analysis calcd. for $C_{12}H_{22}N_2O_5S$: C, 47.04; H, 7.24; N, 9.14; S, 10.46. Found: C, 47.08; H, 7.22; N, 9.06; S, 10.50.

Concentration of the filtrate, followed by trituration with diethyl ether and column chromatography on silica gel, afforded 5.7 g of additional title compound.

Preparation 5 t-butoxycarbonyl-D-methionylglycyl-N-(2-adamantyl)-L-phenylalaninamide hemihydrate The title compound was prepared by the general method of Preparation 1 using the title products of Preparation 2 (37.3 g, 0.11 mole) and Preparation 4 (35.0 g, 0.11 mole) in 250 ml of dichloromethane. The title compound was obtained as an analytically pure solid, m.p. 97°–102°, without further purification.

$[\alpha]_D$ −14.1°; $[\alpha]_{365}$ −46.9° (chloroform).

Analysis calcd. for $C_{31}H_{46}N_4O_5S \cdot \frac{1}{2}H_2O$: C, 62.49; H, 7.95; N, 9.40; S, 5.38. Found: C, 62.78; H, 7.91; N, 9.36; S, 5.60.

Preparation 6

D-methionylglycyl-N-(2-adamantyl)-L-phenylalaninamide hydrochloride hydrate

The title compound (17.4 g) was prepared by the method of Preparation 2 using 20.0 g (0.034 mole) of the title product of Preparation 5.

Analysis calcd. for $C_{26}H_{38}N_4O_3S \cdot HCl \cdot H_2O$: C, 57.70; H, 7.63; N, 10.35; S, 5.92. Found: C, 57.16; H, 7.55; N, 10.19; S, 6.01.

Preparation 7

S-benzyl-D-cysteinylglycyl-N-(2-adamantyl)-L-phenylalaninamide hydrochloride

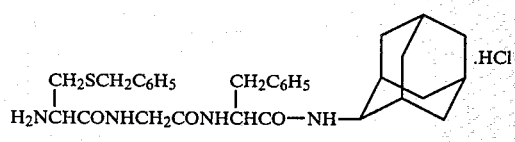

The title compound was prepared by the methods of Preparations 1, 2, 5, and 6 using t-butoxycarbonyl-S-benzylcysteine instead of t-butoxycarbonyl-D-methionine. The title compound was used in subsequent reactions without further characterization.

Preparation 8 t-butoxycarbonyl-2-methyl-D,L-leucine

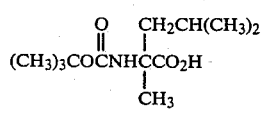

To 4.35 g (30 mmole) of α-methyl-D,L-leucine dissolved in 30 ml each of 1M aqueous sodium hydroxide and t-butyl alcohol was added 7.6 ml (ca. 33 mmole) of di-t-butyl dicarbonate. After overnight stirring, the mixture was diluted with water and washed with two portions of pentane. The aqueous layer was acidified with 5% citric acid and extracted with three portions of ethyl acetate. The organic layers were combined and dried over magnesium sulfate, filtered, and concentrated in vacuo to dryness. The oily residue solidified to give 3.9 g of the title compound as a white solid, which was used in subsequent reactions without further purification.

Preparation 9 t-butoxycarbonyl-3-cyclohexyl-N-ethyl-L-alanine

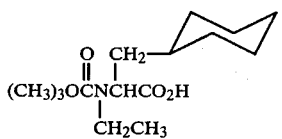

To a mixture of 2.65 g (10 mmole) of Boc-Phe in 50 ml of cold (ca. −78°), dry tetrahydrofuran was added 12 ml (ca. 22 mmole) of 1.9M t-butyllithium. After thirty minutes, the mixture was allowed to warm to −20° and then to react with 4.2 g (22 mmole) of triethyloxonium tetrafluoroborate. After thirty minutes, the mixture was allowed to warm to 0° and was then poured into water and extracted with dichloromethane. The organic extract was washed sequentially with portions of 5% aqueous sodium bicarbonate and water, dried over sodium sulfate, filtered, and concentrated to dryness. Distillation (ca. 130°–200°) afforded an oil that was further purified by column chromatography on silica gel to give t-butoxycarbonyl-N-ethylphenylalanine ethyl ester. To a stirred mixture of this ester intermediate in tetrahydrofuran was added a two-fold (molar) quantity of potassium hydroxide in water. After the mixture was stirred overnight, an equal volume of dichloromethane was added and acidified to pH 3 with 0.5M sodium bisulfate. The aqueous layer was separated and washed with dichloromethane, and all organic layers were recombined. This organic solution was further washed with water, dried over sodium sulfate, filtered, and concentrated in vacuo to dryness. Column chromatography on silica gel afforded de-esterified t-butoxycarbonyl-N-ethylalanine. A solution of 2.6 g of this protected amino acid intermediate in about 100 ml of tetrahydrofuran was catalytically hydrogenated at 80° using 60 psi hydrogen gas and 5% rhodium on carbon. The mixture was filtered and the filtrate was concentrated to an oil which crystallized on standing to afford 2.0 g of the title compound. The title compound was used in subsequent reactions without further purification.

$[\alpha]_D$ −36.5°; $[\alpha]_{365}$ −136.5° (chloroform).

DESCRIPTION OF THE EMBODIMENTS

Example 1

3-cyclohexyl-L-alanyl-D-methionylglycyl-N-(2-adamantyl)-L-phenylalaninamide hydrochloride hemihydrate

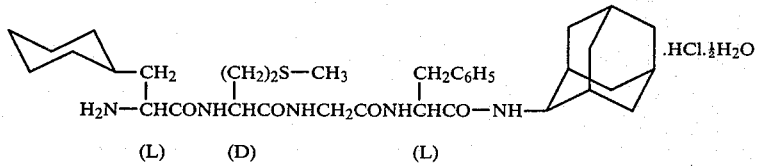

The N-terminal t-butoxycarbonyl-protected derivative of the title compound was prepared by the general method described in Preparation 1 using 0.87 g (3.2 mmole) of t-butoxycarbonyl-3-cyclohexyl-L-alanine and the title product of Preparation 6 (1.2 g, 2.3 mmole) in 60 ml of tetrahydrofuran. The crude intermediate (700 mg) was purified by chromatography on silica gel. The title product (600 mg) was then prepared from this intermediate using the method described in Preparation 2.

Analysis calcd. for $C_{35}H_{53}N_5O_4S \cdot HCl \cdot H_2O$: C, 61.34; H, 8.09; N, 10.22; S, 4.68. Found: C, 61.56; H, 8.05; N, 10.25; S, 4.70.

Example 2

L-leucyl-D-methionylglycyl-N-(2-adamantyl)-L-phenylalaninamide hydrochloride

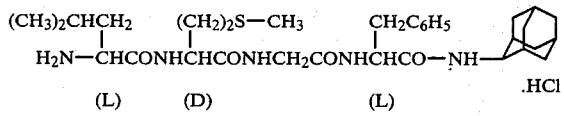

The title compound (1.1 g) was prepared by the method described in Example 1 using t-butoxycarbonyl-L-leucine instead of t-butoxycarbonyl-3-cyclohexyl-L-alanine.

Analysis calcd. for $C_{32}H_{49}N_5O_4S \cdot HCl$: C, 60.40; H, 7.92; N, 11.01; S, 5.04. Found: C, 59.98; H, 7.87; N, 10.93; S, 5.01.

Example 3

L-isoleucyl-D-methionylglycyl-N-(2-adamantyl)-L-phenylalaninamide hydrochloride

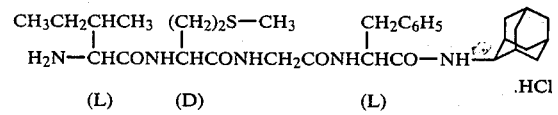

The title compound (1.0 g) was prepared by the method desribed in Example 1 using t-butoxycarbonyl-L-isoleucine instead of t-butoxycarbonyl-3-cyclohexyl-L-alanine and dichloromethane as solvent instead of tetrahydrofuran.

t-butoxycarbonyl intermediate: $[\alpha]_D$ −47.7°; $[\alpha]_{365}$ −136.6° (methanol).

Analysis calcd. for $C_{37}H_{59}N_5O_6S$: C, 63.48; H, 8.21; N, 10.00; S, 4.58. Found: C, 63.63; H, 8.11; N, 9.95; S, 4.68.

Title compound: [α]$_D$ +14.3°; [α]$_{365}$ +41.9° (methanol).

Analysis calcd. for C$_{32}$H$_{49}$N$_5$O$_4$S.HCl: C, 60.40; H, 7.92; N, 11.01; S, 5.04; Cl, 5.57. Found: C, 60.21; H, 7.83; N, 10.92; S, 4.96; Cl, 5.81.

Example 4

L-valyl-D-methionylglycyl-N-(2-adamantyl)-L-phenylalaninamide hydrochloride ¼ hydrate

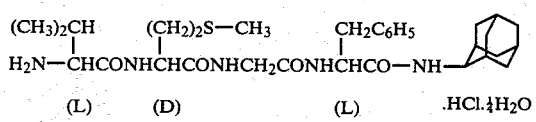

The title compound (3.1 g) was prepared by the method described in Example 1 using t-butoxycarbonyl-L-valine instead of t-butoxycarbonyl-3-cyclohexyl-L-alanine and dichloromethane as solvent instead of tetrahydrofuran.

t-butoxycarbonyl intermediate: [α]$_D$ +2.9°; [α]$_{365}$ +13.3° (chloroform).

Analysis calcd. for C$_{36}$H$_{55}$N$_5$O$_6$S: C, 63.04; H, 8.04; N, 10.21; S, 4.67. Found: C, 62.82; H, 8.03; N, 9.97; S, 4.65.

Title compound: [α]$_D$ +4.7°; [α]$_{365}$ +17.7° (methanol)

Analysis calcd. for C$_{31}$H$_{47}$N$_5$O$_4$S.HCl.¼H$_2$O; C, 59.40; H, 7.80; N, 11.17; S, 5.12; Cl, 5.66. Found: C, 59.23; H, 7.71; N, 11.07; S, 5.13; Cl, 5.76.

Example 5

2-methyl-D,L-leucyl-D-methionylglycyl-N-(2-adamantyl)-L-phenylalaninamide hydrochloride hemihydrate

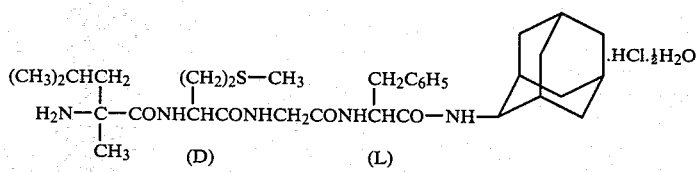

The title compound (1.1 g) was prepared by the method described in Example 1 using t-butoxycarbonyl-2-methyl-D,L-leucine instead of t-butoxycarbonyl-3-cyclohexyl-L-alanine. Analysis calcd. for C$_{33}$H$_{51}$N$_5$O$_4$S.HCl.½H$_2$O: C, 60.12; H, 8.10; N, 10.62; S, 4.86. Found: C, 59.74; H, 7.90; N, 10.47; S, 4.82.

Example 6

3-cyclohexyl-N$^α$-ethyl-L-alanyl-D-methionylglycyl-N-(2-adamantyl)-L-phenylalaninamide hydrochloride hemihydrate

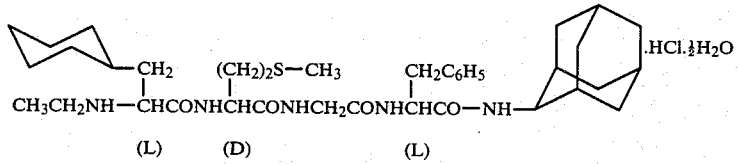

The title compound (586 mg) was prepared by the method described in Example 1 using the title product of Preparation 9 instead of t-butoxycarbonyl-3-cyclohexyl-L-alanine and dichloromethane as solvent instead of tetrahydrofuran.

t-butoxycarbonyl intermediate: [α]$_D$ −37.0°; [α]$_{365}$ −152.0° (chloroform).

Analysis calcd. for C$_{42}$H$_{65}$N$_5$O$_6$S: C, 65.68; H, 8.53; N, 9.12; S, 4.17. Found: C, 66.03; H, 8.66; N, 8.88; S, 4.15.

Title compound: [α]$_D$ +19.1°; [α]$_{365}$ +54.8° (methanol).

Analysis calcd. for C$_{37}$H$_{57}$N$_5$O$_4$S.HCl.½H$_2$O: C, 62.29; H, 8.34; N, 9.82; S, 4.49; Cl, 4.97. Found: C, 62.08; H, 8.13; N, 9.77; S, 4.55; Cl, 5.17.

EXAMPLE 7

3-cyclohexyl-L-alanyl-S-benzyl-D-cysteinylglycyl-N-(2-adamantyl)-L-phenylalaninamide hydrochloride hemihydrate

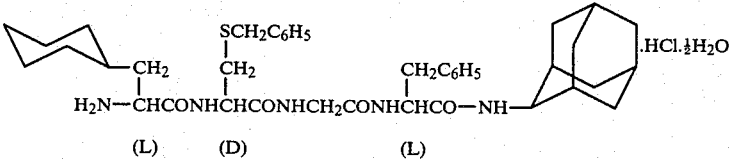

The title compound was prepared by the method described in Example 1 using the title product of Preparation 7 instead of the title product of Preparation 6.

Title compound: Analysis calcd. for C$_{40}$H$_{55}$N$_5$O$_4$S.HCl: C, 65.06; H, 7.64; N, 9.49. Found: C, 64.84; H, 7.62; N, 9.48.

EXAMPLE 8

3-cyclohexyl-L-alanyl-[4-(methylsulfinyl)-D-2-aminobutanoyl]glycyl-N-(2-adamantyl)-L-phenylalaninamide hydrochloride hemihydrate

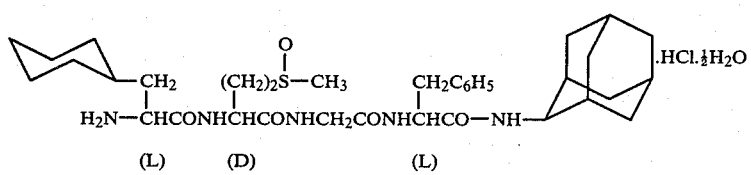

To a solution of the title product of Example 1 (0.10 g, 0.15 mmole) in 5 ml of methanol was added 0.5 ml of 30% aqueous hydrogen peroxide. After about 90 minutes at room temperature, the reaction mixture was concentrated in vacuo and the residue was lyophilized overnight. The title compound was obtained as 93 mg of a pure white solid.

Analysis calcd. for $C_{35}H_{53}N_5O_5S.HCl.\frac{1}{2}H_2O$: C, 59.93; H, 7.90; N, 9.98; S, 4.57. Found: C, 60.01; H, 7.89; N, 10.12; S, 4.48.

EXAMPLE 9

L-leucyl-[4-(methylsulfinyl)-D-2-aminobutanoyl]-glycyl-N-(2-adamantyl)-L-phenylalaninamide hydrochloride hydrate

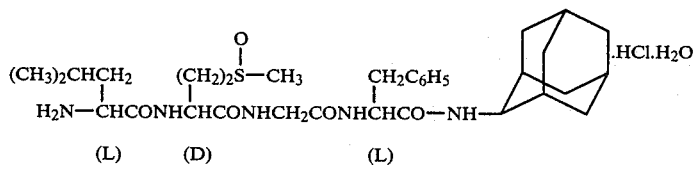

The title compound (175 mg) was prepared by the method described in Example 8 using the title product of Example 2.

Analysis calcd. for $C_{32}H_{49}N_5O_5S.HCl.H_2O$: C, 57.34; H, 7.82; N, 10.45; S, 4.78. Found: C, 57.28; H, 7.69; N, 10.36; S, 4.71.

EXAMPLE 10

L-isoleucyl-[4-(methylsulfinyl)-D-2-aminobutanoyl]glycyl-N-(2-adamantyl)-L-phenylalaninamide hydrochloride hemihydrate

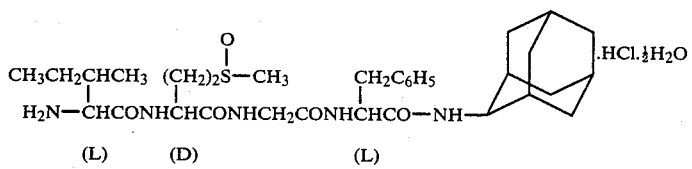

The title compound (0.90 g) was prepared by the method described in Example 8 using the title product of Example 3, except that solidification was effected by trituration with diethyl ether rather than by lyophilization.

$[\alpha]_D + 9.2°$; $[\alpha]_{365} + 30.8°$ (methanol)

Analysis calcd. for $C_{32}H_{49}N_5O_5S.HCl$: C, 58.11; H, 7.77; N, 10.59; S, 4.84; Cl 5.36. Found: C, 58.07; H, 7.72; N, 10.44; S, 4.82; Cl, 5.40.

EXAMPLE 11

L-valyl-D-[4-(methylsulfinyl)-D-2-aminobutanoyl]-glycyl-N-(2-adamantyl)-L-phenylalaninamide hydrochloride hemihydrate

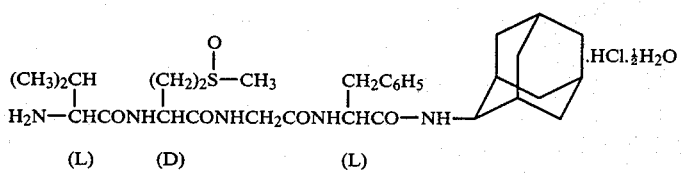

The title compound (1.30 g) was prepared by the method described in Example 8 using the title product of Example 4, except that solidification was effected by trituration with diethyl ether rather than by lyophilization.

$[\alpha]_D + 0.9°$; $[\alpha]_{365} + 16.5°$ (methanol).

Analysis calcd. for $C_{31}H_{47}N_5O_5S.HCl.\frac{1}{2}H_2O$: C, 57.52; H, 7.63; N, 10.82; S, 4.95; Cl, 5.48. Found: C, 57.35; H, 7.62; N, 10.66; S, 5.01; Cl, 5.36.

EXAMPLE 12

L-leucyl-D-methionylglycyl-N-(2-adamantyl)-L-phenylalaninamide

The title product of Example 2 is stirred under argon in water containing a molar excess of potassium bicarbonate. After about one hour the mixture is extracted with dichloromethane, and the organic layer is dried over sodium sulfate, filtered, and concentrated in vacuo to produce the title compound as the free base.

What is claimed is:

1. A compound of the formula:

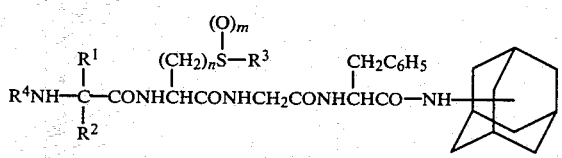

wherein R¹ is:

(a)

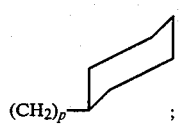

or (b) straight or branched chain alkyl of 1 to 6 carbon atoms, inclusive;

wherein R² is:

(a) hydrogen; or (b) alkyl of 1 to 3 carbon atoms, inclusive;

wherein R³ is:

(a) $CH_2C_6H_5$; or (b) alkyl of 1 to 3 carbon atoms, inclusive.

wherein R⁴ is:

(a) hydrogen; or (b) alkyl of 1 to 6 carbon atoms, inclusive;

wherein m is 0, 1, or 2;

wherein n is 1 or 2;

wherein p is 0, 1, or 2;

and the stereochemical configuration of each of the optically active amino acid residues may independently be D, L or DL; and the pharmaceutically acceptable salts thereof.

2. A compound according to claim 1 having the formula:

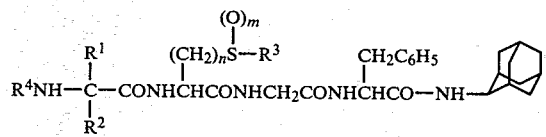

wherein R¹ is:

(a)

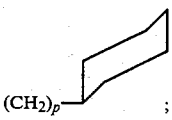

or (b) straight or branched chain alkyl of 1 to 6 carbon atoms, inclusive;

wherein R² is:

(a) hydrogen; or (b) alkyl of 1 to 3 carbon atoms, inclusive;

wherein R³ is:

(a) $CH_2C_6H_5$; or (b) alkyl of 1 to 3 carbon atoms, inclusive;

wherein R⁴ is:

(a) hydrogen; or (b) alkyl of 1 to 6 carbon atoms, inclusive;

wherein m is 0, 1, or 2;

wherein n is 1 or 2;

wherein p is 0, 1, or 2;

and the stereochemical configuration of each of the optically active amino acid residues independently be D, L or DL; and the pharmaceutically acceptable salts thereof.

3. A compound according to claim 2 having the formula:

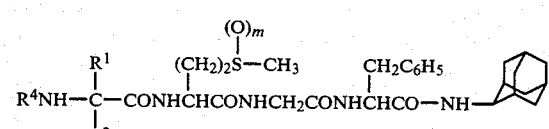

wherein R¹ is:

(a)

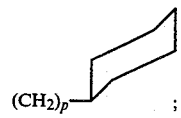

or (b) straight or branched chain alkyl of 1 to 6 carbon atoms, inclusive;

wherein R² is:

(a) hydrogen; or (b) alkyl of 1 to 3 carbon atoms, inclusive;

wherein R⁴ is:

(a) hydrogen; or (b) alkyl of 1 to 6 carbon atoms, inclusive;

wherein m is 0, 1, or 2;

wherein p is 0, 1, or 2;

and the stereochemical configuration of each of the optically active amino acid residues may independently be D, L or DL; and the pharmaceutically acceptable salts thereof.

4. A compound according to claim 3 having the formula:

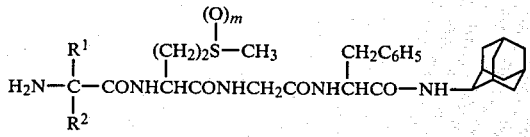

wherein R¹ is:

(a)

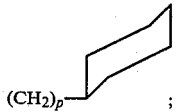

or (b) straight or branched chain alkyl of 1 to 6 carbon atoms, inclusive;

wherein R² is:

(a) hydrogen; or (b) alkyl of 1 to 3 carbon atoms, inclusive;
wherein m is 0, 1, or 2;
wherein p is 0, 1, or 2;
and the stereochemical configuration of each of the optically active amino acid residues may independently be D, L or DL; and the pharmaceutically acceptable salts thereof.

5. A compound according to claim 4 having the formula:

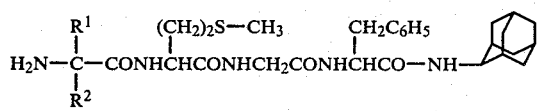

wherein R¹ is:
(a)

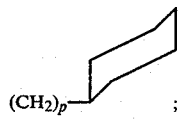

or
(b) straight or branched chain alkyl of 1 to 6 carbon atoms, inclusive;
wherein R² is:
(a) hydrogen; or
(b) alkyl of 1 to 3 carbon atoms, inclusive;
wherein p is 0, 1, or 2;
and the stereochemical configuration of each of the optically active amino acid residues may independently be D, L or DL; and the pharmaceutically acceptable salts thereof.

6. A compound according to claim 5 having the formula:

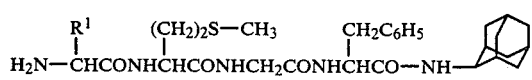

wherein R¹ is:
(a)

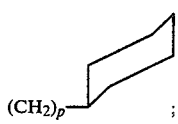

or
(b) straight or branched chain alkyl of 1 to 6 carbon atoms, inclusive;
wherein p is 0, 1, or 2;
and the stereochemical configuration of each of the optically active amino acid residues may independently be D, L or DL; and the pharmaceutically acceptable salts thereof.

7. A compound according to claim 6 having the formula:

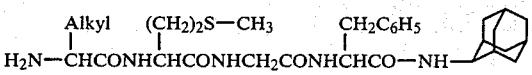

and the stereochemical configuration of each of the optically active amino acid residues may independently be D, L or DL; and the pharmaceutically acceptable salts thereof.

8. A compound according to claim 7, which is L-leucyl-D-methionylglycyl-N-(2-adamantyl)-L-phenylalaninamide.

9. A compound according to claim 7, which is L-isoleucyl-D-methionylglycyl-N-(2-adamantyl)-L-phenylalaninamide.

10. A compound according to claim 7, which is L-valyl-D-methionylglycyl-N-(2-adamantyl)-L-phenylalaninamide.

11. A compound according to claim 6 having the formula:

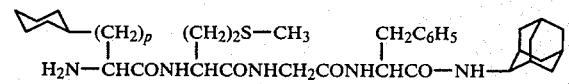

wherein p is 0, 1, or 2;
and the stereochemical configuration of each of the optically active amino acid residues may independently be D, L or DL; and the pharmaceutically acceptable salts thereof.

12. A compound according to claim 11, which is 3-cyclohexyl-L-alanyl-D-methionylglycyl-N-(2-adamantyl)-L-phenylalaninamide.

13. A compound according to claim 5 having the formula:

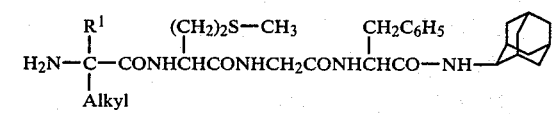

wherein R¹ is:
(a)

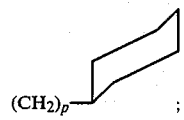

or
(b) straight or branched chain alkyl of 1 to 6 carbon atoms, inclusive;
wherein p is 0, 1, or 2;
and the stereochemical configuration of each of the optically active amino acid residues may independently be D, L or DL; and the pharmaceutically acceptable salts thereof.

14. A compound according to claim 13, which is 2-methyl-D,L-leucyl-D-methionylglycyl-N-(2-adamantyl)-L-phenylalaninamide.

15. A compound according to claim 4 having the formula:

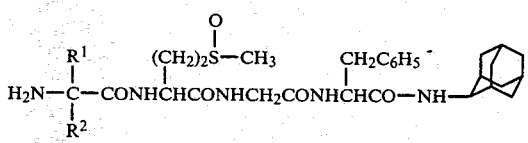

wherein R¹ is:
(a)

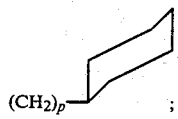

or (b) straight or branched chain alkyl of 1 to 6 carbon atoms, inclusive;

wherein R² is:
(a) hydrogen; or
(b) alkyl of 1 to 3 carbon atoms, inclusive;

wherein p is 0, 1, or 2;
and the stereochemical configuration of each of the optically active amino acid residues may independently be D, L or DL; and the pharmaceutically acceptable salts thereof.

16. A compound according to claim 15, which is L-leucyl-[4-(methylsulfinyl)-D-2-aminobutanoyl]glycyl-N-(2-adamantyl)-L-phenylalaninamide.

17. A compound according to claim 15, which is L-isoleucyl-[4-(methylsulfinyl)-D-2-aminobutanoyl]glycyl-N-(2-adamantyl)-L-phenylalaninamide.

18. A compound according to claim 15, which is L-valyl-D-[4-(methylsulfinyl)-D-2-aminobutanoyl]glycyl-N-(2-adamantyl)-L-phenylalaninamide.

19. A compound according to claim 15, which is 3-cyclohexyl-L-alanyl-[4-(methylsulfinyl)-D-2-aminobutanoyl]glycyl-N-(2-adamantyl)-L-phenylalaninamide.

20. A compound according to claim 2 having the formula:

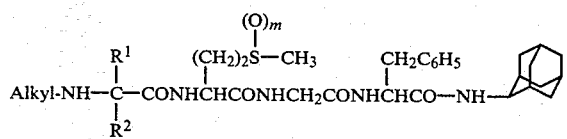

wherein R¹ is:
(a)

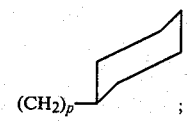

or (b) straight or branched chain alkyl of 1 to 6 carbon atoms, inclusive;

wherein R² is:
(a) hydrogen; or
(b) alkyl of 1 to 3 carbon atoms, inclusive;

wherein m is 0, 1, or 2;
wherein p is 0, 1, or 2;
and the stereochemical configuration of each of the optically active amino acid residues may independently be D, L or DL; and the pharmaceutically acceptable salts thereof.

21. A compound according to claim 15, which is 3-cyclohexyl-Nα-ethyl-L-alanyl-D-methionylglycyl-N-(2-adamantyl)-L-phenylalaninamide.

22. A compound according to claim 2 having the formula:

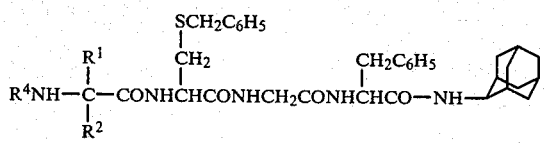

wherein R¹ is:
(a)

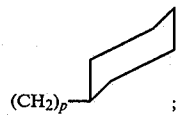

or (b) straight or branched chain alkyl of 1 to 6 carbon atoms, inclusive;

wherein R² is:
(a) hydrogen; or
(b) alkyl of 1 to 3 carbon atoms, inclusive;

wherein R⁴ is:
(a) hydrogen; or
(b) alkyl of 1 to 6 carbon atoms, inclusive;

wherein m is 0, 1, or 2;
wherein p is 0, 1, or 2;
and the stereochemical configuration of each of the optically active amino acid residues may independently be D, L or DL; and the pharmaceutically acceptable salts thereof.

23. A compound according to claim 21, which is 3-cyclohexyl-L-alanyl-S-benzyl-D-cysteinylglycyl-N-(2-adamantyl)-L-phenylalaninamide.

* * * * *